US010892907B2

(12) United States Patent
Gould et al.

(10) Patent No.: US 10,892,907 B2
(45) Date of Patent: Jan. 12, 2021

(54) HOME AUTOMATION SYSTEM INCLUDING USER INTERFACE OPERATION ACCORDING TO USER COGNITIVE LEVEL AND RELATED METHODS

(71) Applicant: K4CONNECT INC., Raleigh, NC (US)

(72) Inventors: Jonathan Andrew Gould, Raleigh, NC (US); Richard Clancy, Pittsboro, NC (US); Robert Shannon Smith, Raleigh, NC (US)

(73) Assignee: K4CONNECT INC., Raleigh, NC (US)

( * ) Notice: Subject to any disclaimer, the term of this patent is extended or adjusted under 35 U.S.C. 154(b) by 0 days.

(21) Appl. No.: 16/176,315

(22) Filed: Oct. 31, 2018

(65) Prior Publication Data
US 2019/0182071 A1 Jun. 13, 2019

Related U.S. Application Data

(60) Provisional application No. 62/595,810, filed on Dec. 7, 2017.

(51) Int. Cl.
| | |
|---|---|
| *H04L 12/28* | (2006.01) |
| *G06F 3/0484* | (2013.01) |
| *G06F 3/0488* | (2013.01) |
| *A61B 5/00* | (2006.01) |
| *A61B 5/11* | (2006.01) |
| *A63F 13/23* | (2014.01) |
| *H04L 29/08* | (2006.01) |

(Continued)

(52) U.S. Cl.
CPC ........ *H04L 12/2803* (2013.01); *A61B 5/0022* (2013.01); *A61B 5/1113* (2013.01); *A61B 5/4088* (2013.01); *A61B 5/4842* (2013.01); *G06F 3/0484* (2013.01); *G06F 3/0488* (2013.01); *A61B 5/1101* (2013.01);
(Continued)

(58) Field of Classification Search
None
See application file for complete search history.

(56) References Cited

U.S. PATENT DOCUMENTS

| | | |
|---|---|---|
| 7,849,115 B2 | 12/2010 | Reiner |
| 8,020,104 B2 | 9/2011 | Robarts et al. |

(Continued)

FOREIGN PATENT DOCUMENTS

WO 2014105782 A1 7/2014

OTHER PUBLICATIONS

Patrick Moorhead, The Problem With Home Automation's Internet of Things (IoT), Forbes, Sep. 26, 2013.

*Primary Examiner* — Christopher J Fibbi
(74) *Attorney, Agent, or Firm* — Allen, Dyer, Doppelt + Gilchrist, P.A.

(57) ABSTRACT

A home automation (HA) system may include a cloud server, HA operation devices within a senior living facility, and HA user interface devices for respective users within the senior living facility. Each HA user interface device may include a user input device, a display defining a user interface (UI), and a controller. The HA system may include HA hub devices within the senior living facility to provide communications for the cloud server, the HA user interface devices, and the HA operation devices. The controller may send user interaction data to the cloud server and operate the UI according to a user cognitive level. The cloud server may be configured to determine the user cognitive level based upon the user interaction data received from a given HA user interface device, and send the user cognitive level to the given HA user interface device.

20 Claims, 7 Drawing Sheets

(51) Int. Cl.
  *G06T 7/50* (2017.01)
  *A63F 13/25* (2014.01)
  *A61B 5/16* (2006.01)

(52) U.S. Cl.
  CPC .......... *A61B 5/16* (2013.01); *A61B 5/746* (2013.01); *A61B 2503/08* (2013.01); *A61B 2505/07* (2013.01); *A63F 13/23* (2014.09); *A63F 13/25* (2014.09); *A63F 2300/308* (2013.01); *G06T 7/50* (2017.01); *H04L 67/12* (2013.01)

(56) References Cited

U.S. PATENT DOCUMENTS

| | | |
|---|---|---|
| 2003/0046401 A1 | 3/2003 | Abbott et al. |
| 2006/0139312 A1* | 6/2006 | Sinclair, II ............ G06F 3/0481 345/156 |
| 2009/0300495 A1 | 12/2009 | Brown et al. |
| 2011/0010646 A1* | 1/2011 | Usey .................... A61F 4/00 715/762 |
| 2013/0035117 A1* | 2/2013 | Litkouhi ................ H04L 67/12 455/456.4 |
| 2013/0275875 A1* | 10/2013 | Gruber .................. G06F 3/167 715/728 |
| 2014/0282061 A1* | 9/2014 | Wheatley ............. H04N 21/431 715/745 |
| 2015/0112899 A1* | 4/2015 | Dagum ................. A61B 5/6898 706/12 |
| 2016/0029884 A1* | 2/2016 | Kockan ................. A61B 3/0033 351/239 |
| 2017/0006533 A1 | 1/2017 | Gould et al. |
| 2017/0053540 A1* | 2/2017 | Meagher ................. G09B 5/00 |
| 2017/0132016 A1 | 5/2017 | Zilberman et al. |
| 2018/0342329 A1* | 11/2018 | Rufo .................... G16H 40/67 |

* cited by examiner

HOME AUTOMATION SYSTEM INCLUDING USER INTERFACE OPERATION ACCORDING TO USER COGNITIVE LEVEL AND RELATED METHODS

RELATED APPLICATION

The present application is based upon provisional application Ser. No. 62/595,810, filed Dec. 7, 2017, the entire contents of which is hereby incorporated by reference.

TECHNICAL FIELD

The present embodiments are directed to the field of electronics, and more particularly to home automation systems and related methods.

BACKGROUND

There are a number of home automation systems and approaches that seek to permit automated control of electrical devices in a house. The popularity of home automation has been increasing due to the greater availability of smartphones and tablets. As noted in "The Problem With Home Automation's Internet Of Things (IoT)", an article appearing in Forbes dated Sep. 26, 2013, home automation was typically for wealthy consumers with an expensive system to control lights, home theater, security, air conditioning, and home audio. This market has expanded with many do it yourself (DIY) products now available, and, although the products are useful, they may be difficult to aggregate. In other words, as explained in the article, difficulties could arise if a consumer bought a Nest thermostat, Kwikset door lock, Phillips Hue lighting device, Lutron light switch, Sonos audio system, and Belkin wireless plugs. The consumer would need to have multiple applications each requiring time to setup, learn, and use. Additionally, the article states that there is no easy way to make devices work together, such as if the consumer wanted to trigger one event using one device based on another event from another device.

Multiple communication protocols may also be problematic. In particular, different devices may operate using different communication protocols, for example, Wifi, Zigbee, Zwave, Insteon, Itron, RadioRA2, and others. This may create additional difficulties for home automation.

One approach to address these shortcomings is for the consumer, which may include a user and/or enterprise, to use a service and device aggregator that provides one application and a consolidated wireless adapter unit. The user would contract with such a provider for multiple years. Unfortunately, as noted in the article, the consumer may not benefit from the most advanced hardware and software.

Another approach, as noted in the Forbes article, is to provide a single application that attempts to consolidate disparate applications and consolidate wireless adaptors, for example, using each of the different communications protocols. However, such aggregation or single application approaches may present increased difficulty in usability. For example, if a given user cannot readily operate the one application or if the application is not readily accessible for any given user, operational difficulties may still exist. Accordingly, further improvements to the operation of home automation devices may be desirable.

SUMMARY

A home automation (HA) system may include a cloud server, a plurality of HA operation devices within a senior living facility, and a plurality of HA user interface devices for respective users within the senior living facility. Each of the plurality of HA user interface devices may include a user input device, a display defining a user interface (UI), and a controller coupled to the user input device and the display. The HA system may also include a plurality of HA hub devices within the senior living facility to provide communications for the cloud server, the plurality of HA user interface devices and the plurality of HA operation devices. The controller of each HA user interface device may be configured to send user interaction data to the cloud server and operate the UI according to a user cognitive level. The cloud server may be configured to determine a cognitive level of the user based upon the user interaction data received from a given HA user interface device and send the user cognitive level to the given HA user interface device.

The cloud server may be configured to decrease the user cognitive level based upon the user interaction data received from the given HA user interface device representing cognitive decline of the user, for example. The display and the input device may define a touch display, and the controller of each HA user interface device may be configured to acquire user interaction data from the touch display.

The user interaction data may include touch display user contact data. The user interaction data may include time periods between successive user contacts, for example.

The user input device may include a camera, and the user interaction data may include device-to-user distance data. The user input device may include an accelerometer, and the user interaction data may include device acceleration data, for example.

The user interaction data may include user game interaction data. The user cognitive level may determine at least one of a color adjustment within the UI, an adjustment in contrast within the UI, an adjustment in brightness within the UI, an adjustment in size within the UI, and a disablement of elements within the UI, for example.

A method aspect is directed to a method of operating a user interface (UI) according to a user cognitive level. The UI is defined by a display of a given home automation (HA) user interface device for a respective user within a senior living facility from among a plurality of HA user interface devices in an HA system. The HA system includes a cloud server, a plurality of HA operation devices within the senior living facility, and a plurality of HA hub devices within the senior living facility to provide communications for the cloud server, the plurality of HA user interface devices and the plurality of HA operation devices. The method may include using the HA user interface device to send user interaction data to the cloud server, the cloud server determining the user cognitive level based upon the user interaction data and to receive the user cognitive level from the cloud server. The method may also include using the HA user interface device to operate the UI according to the user cognitive level.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Figure 1:
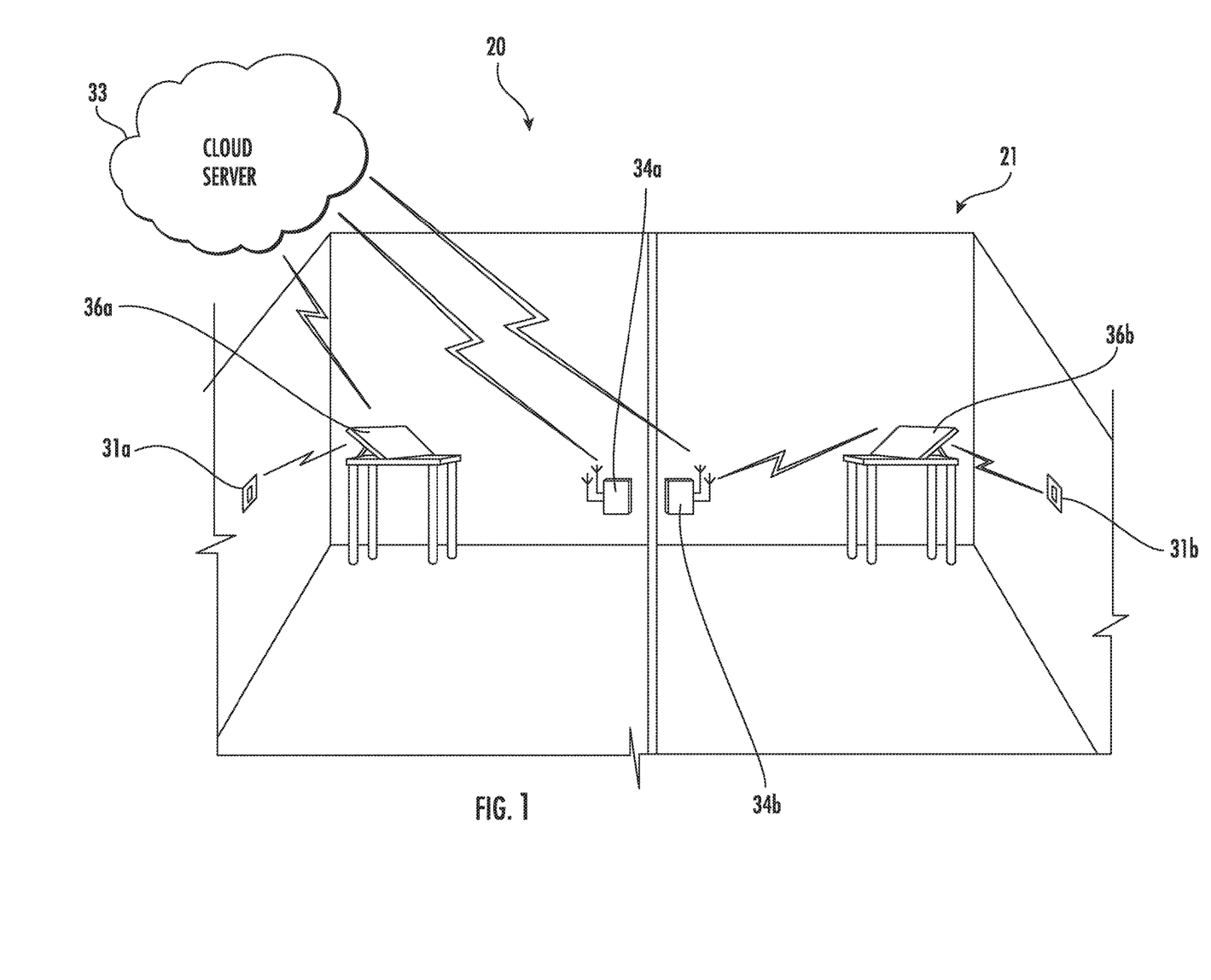
FIG. 1 is a diagram of a structure including an HA system in accordance with an embodiment.
Figure 2:
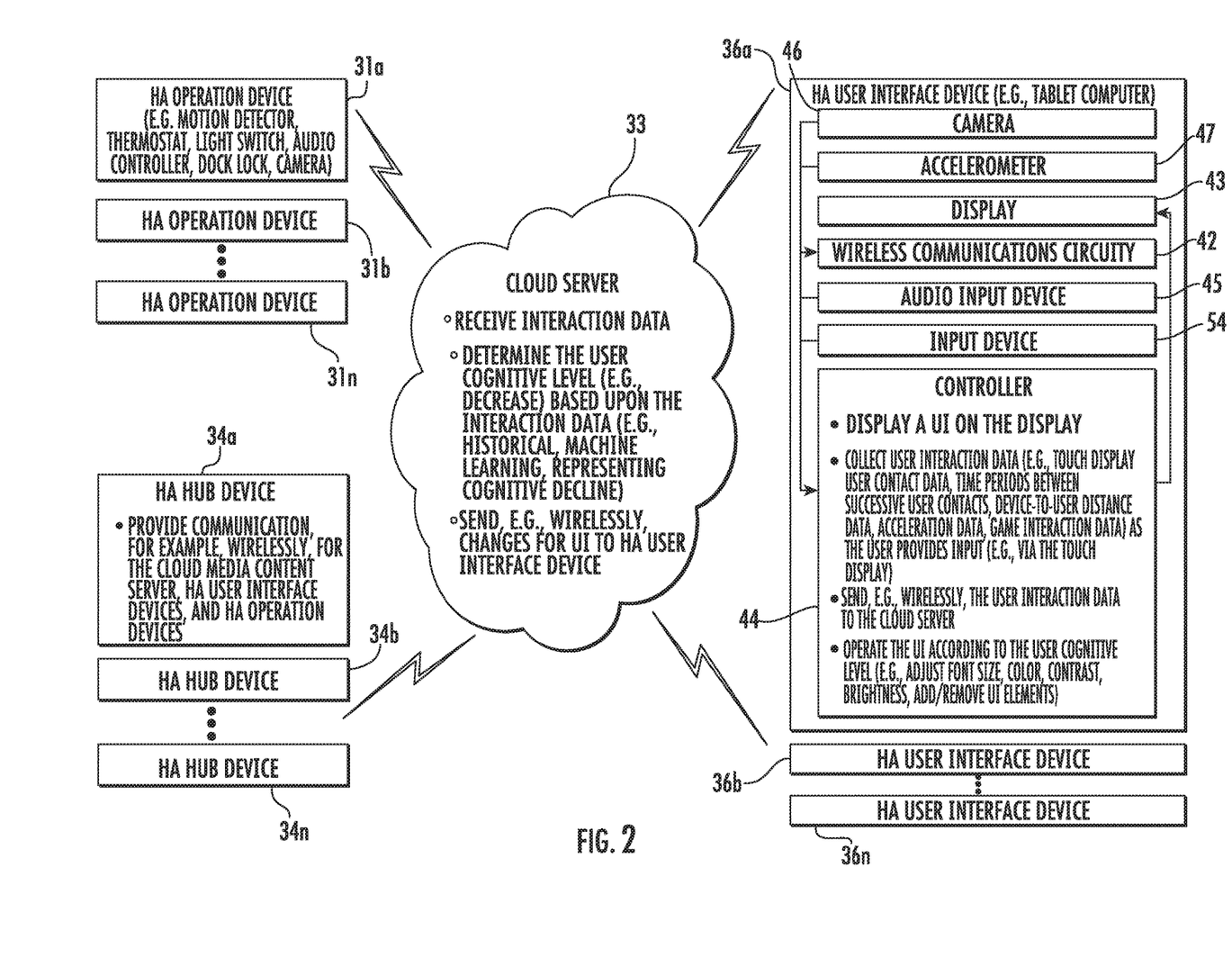
FIG. 2 is a schematic diagram of the HA system of FIG.

Referring initially to FIGS. 1 and 2, a home automation (HA) system 20 illustratively includes a cloud server 33. The cloud server 33 may store media content for distribution, for example, documents, photos, videos, data feeds, etc. The cloud server 33 may also process operations for HA devices, as will be described in further detail below. The cloud server 33 may also function as a gateway to permit operation of HA operation devices 31a-31n from outside a structure 21 or internal network (i.e., over the Internet).

The HA operation devices 31a-31n of the HA system 20 are within the structure 21. The structure 21 may be a senior living facility, for example, and include living rooms for members of the senior living facility. Of course, the structure 21 may be another type of structure, for example, a hospital, a home, a commercial, residential, and/or educational campus, etc.

The HA operation devices 31a-31n may include a light switch in a room in the structure 21, a thermostat, a motion detector, an audio controller, a door lock, and a camera, for example. The HA operation devices 31a-31n may include other and/or additional types of devices.

The HA system 20 also includes HA user interface devices 36a-36n for respective users within the structure 21. The HA user interface devices 36a-36n may be in the form of tablet computers, for example. Each HA user interface device 36a-36n may be another or different type of HA user interface device, for example, a smartphone, a laptop or personal computer, and/or television interface or streaming device.

Each HA user interface device 36a-36n is configured to wirelessly communicate with at least one of the HA operation devices 31a-31n to perform at least one HA operation. For example, a given HA user interface device 36a-36n may be used, based upon input thereto, to control a light switch in a room in the structure 21, control a thermostat, communicate with a motion detector, control an audio controller, control a door lock, and communicate with a camera.

In the exemplary embodiment where an HA user interface device 36a-36n is in the form of a tablet computer, the HA user interface device may include a portable housing 41, wireless communication circuitry 42 carried by the portable housing, an input device 54 carried by the portable housing, and a display 43 carried by the housing. The display 43 and the input device 54 may together define a touch display 55 to accept a touch input. While the embodiments described herein refer to a touch display, it should be understood that embodiments may not include a touch display, but rather a physically separated display 43 and input device 54, such as, for example, a pushbutton. A controller 44 is coupled to the wireless communications circuitry 42 and the display 43. The controller 44 is configured to cooperate with the display 43 to display a user interface (UI) 48, for example, a graphical user interface (GUI). Based upon input to the touch display 55, the controller may cooperate with the wireless communications circuitry 42 to control operation of the HA operation devices 31a-31n. Each HA user interface device 36a-36n may also be used for social media, playing games, and/or surfing the Internet. Each HA user interface device 36a-36n may also provide stored media content to the respective user for listening and/or viewing on a display 43. In the example of a senior living center, the stored media content may include current weather data, a social calendar, a daily food menu for the cafeteria, photos and/or video from a current event, local and national news, etc. Of course, each HA user interface device 36a-36n may be used to perform other and/or additional functions within the HA system 20.

The HA system 20 further includes HA hub devices 34a-34n within the structure or senior living facility 21. The HA hub devices 34a-34n provide communications for the cloud server 33, the HA user interface devices 36a-36n, and the HA operation devices 31a-31n. More particularly, a respective HA hub device 34a-34n may be in each area of the structure 21 and communicate with a corresponding HA user interface device 36a-36n. With respect to the senior living facility example noted above, each member of the senior living facility may have an HA user interface device 36a-36n and an HA hub device 34a-34n within their room. The HA user interface device 36a-36n may communicate with the HA hub device 34a-34n to control respective HA operation devices 31a-31n. The HA hub device 34a-34n may be considered a bridge between respective HA operation devices 31a-31n and the corresponding HA user interface device 36a-36n.

An HA user interface device 36a-36n may communicate with the cloud server 33 to retrieve updated data or media content from the Internet, for example, or uploaded to the cloud server. Of course, the HA user interface device 36a-36n may communicate with either or both of the corresponding HA hub device 34a-34n and cloud server 33 to download or retrieve data and/or media. The HA user interface device 36a-36n may also upload data, for example, to the cloud server 33. With respect to the senior living example, the HA user interface device 36a-36n may upload or communicate usage data and/or other data, for example, cognitive data to be used by staff for determining a user health level and/or a user activity level. Further details of an exemplary HA system are described in U.S. Patent Application Publication No. 2017/0006533, assigned to the present assignee, and the entire contents of which of herein incorporated by reference.

Further details of user interaction with the HA user interface devices 36a-36n, and more particularly, the UI, will now be described. Returning again to the senior living facility example, it may be particularly desirable for staff of the senior living facility to determine if and when a user has undergone a cognitive change, which may be relatively difficult to uncover. For example, a cognitive change may be indicative of a broader health concern. Moreover, a member may be less desirous of using the HA user interface device 36a-36n if they experience operational difficulties due to a cognitive change. To address this, a given user's interaction with the UI 48 of his or her HA user interface device 36a-36n may be used as a basis for adapting the UI. More particularly, the controller 44 of the given HA user interface device 36a-36n operates the UI according to a user cognitive level, as will be described in further detail below, and through the touch display 55 and/or other elements and/or functions of the HA user interface device, monitors interaction with the UI by collecting user interaction data.

Acquired user interaction data may be wirelessly communicated from the given HA user interface device 36a-36n to the cloud server 33 for processing. It should be understood that while functions of the HA user interface devices 36a-36n are described herein, the functions are performed by the controller 44 through cooperation with other respective elements or hardware.

The cloud server 33 may process the acquired user interaction data and communicate with the given HA user interface device 36a-36n to change the UI. More particularly, the cloud server 33 determines the cognitive user level based upon the user interaction data received from the given HA user interface device 36a-36n. The cognitive user level determined by the cloud server 33 may determine how and what UI changes to make based upon historical data for a given member and/or using machine learning techniques, as will be appreciated by those skilled in the art. For example, the cloud server 33 may decrease the user cognitive level based upon the user interaction data being representative over cognitive decline of the user.

Figure 3:
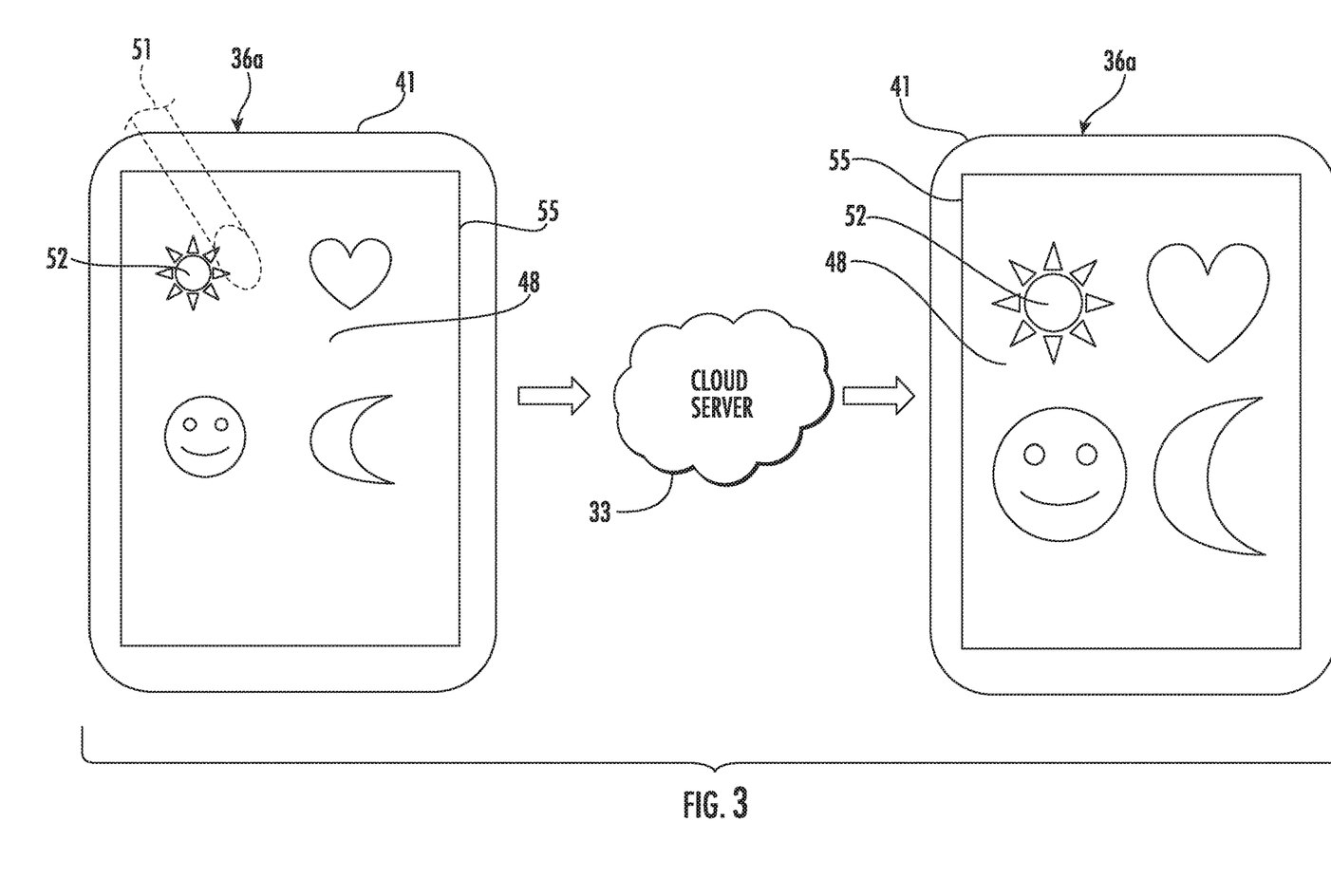
FIG. 3 is an operational diagram of an HA user interface device according to an embodiment.

Various examples of types of changes of the user cognitive level, for example, cognitive decline, and corresponding UI changes will now be described. Referring now additionally to FIG. 3, in one example, the controller 44 may cooperate with the touch display 55 to acquire touch display user contact data. More particularly, an input position of the user 51 on the touch display 55 may be detected. The detected input position may be compared to a position of an element 52 or a "button" displayed on the touch display 55. The detected position and the position of the "button" 52 on the touch display 55 may be communicated to the cloud server 33. The cloud sever 33 may compare the detected position to a historical detected position for the "button" 52. In other words, if the user 51 or member typically presses on the edge of the button 52, the cloud server 33 may determine that the edge press is outside a given tolerance based upon previous inputs and adjust or determine the user cognitive level based thereon. If, for example, the user 51 presses just to the side of the button 52 (but not on it) in several instances (e.g., 3-times), the cloud server 33 may determine the user cognitive level so that the size of the button on the touch display 55 is to be increased (i.e., the user cognitive level determines an adjustment in size in the UI 48).

The cloud server 33 communicates instructions for the HA user interface device 36a to display images, text, and inputs with a larger size. Of course, the cloud server 33 may operate in the reverse. That is, if the detected position of input closely matches the position of the button on the touch display 55, the cloud server 33 may communicate instructions to the HA user interface device 36a to reduce the size of the button on the touch display. As will be appreciated by those skilled in the art, updates to the UI 48 are user dependent rather than machine dependent.

Figure 4:
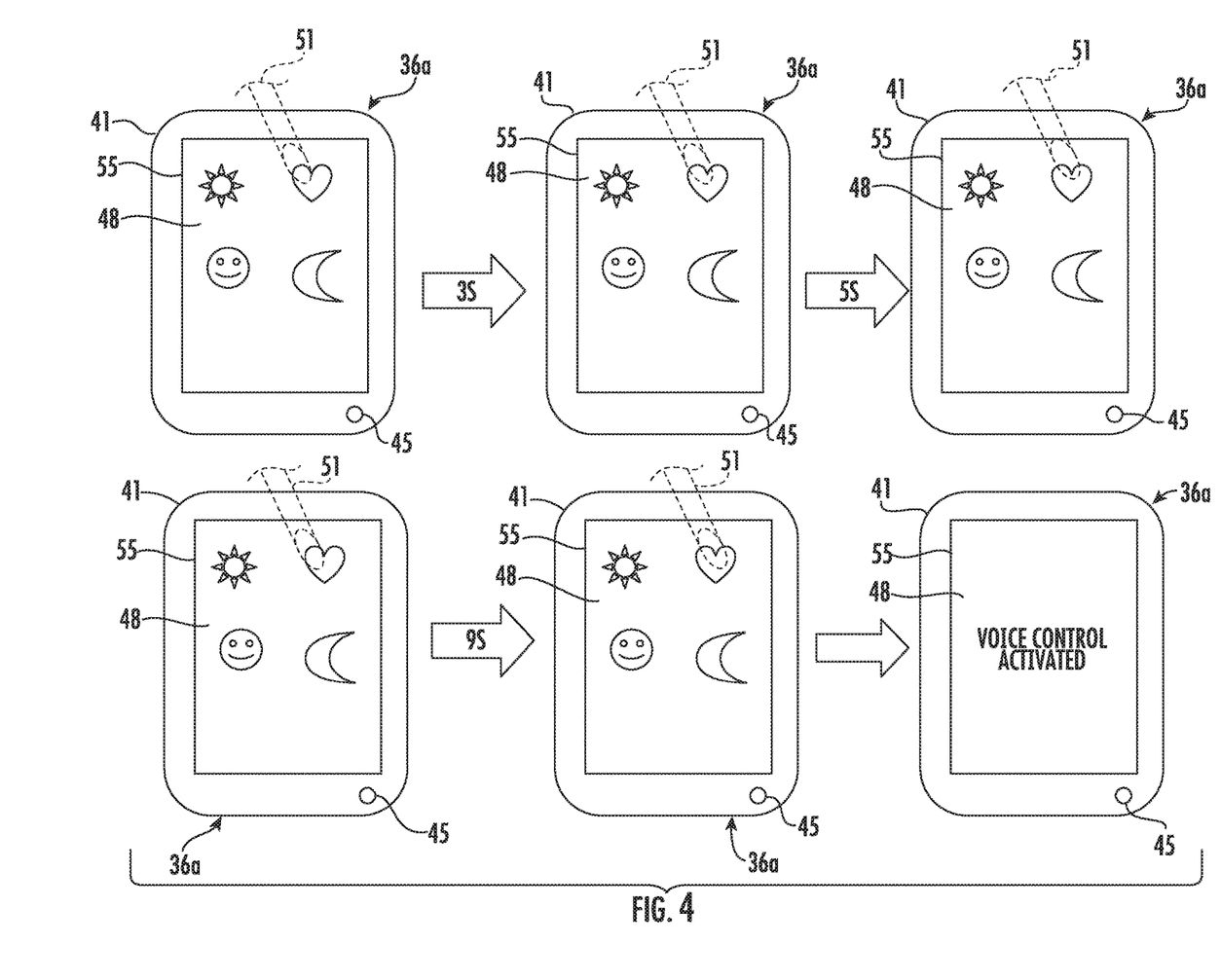
FIG. 4 is an operational diagram of an HA user interface device according to another embodiment.

Referring now additionally to FIG. 4, in another embodiment, a user's typing or input speed may be used as an indicator of cognitive decline. The controller 44 may cooperate with the touch display 55 to detect time periods between successive user contacts (i.e., a time delta between inputs from the user 51 to the touch display). The time between inputs to the touch display 55 may be communicated to the cloud server 33. The cloud sever 33 may compare these time periods to historical time periods between inputs to the touch display 55 to adjust or determine the user cognitive level. If, for example, the time periods between inputs to the touch display 55 are increasing or have increased beyond a threshold time period, the cloud server 33 may determine user cognitive level associated with voice activation instead of typed input should be used. Thus, the cloud server 33 communicates the user cognitive level, for example, wirelessly, that causes the HA user interface device 36a to switch to a voice command mode and/or remove a keyboard (e.g., icons, letters keys, etc.) from the touch display 55. The corresponding HA user interface device 36a may also remove the UI elements 52 or the keyboard from the touch display 55 and begin a voice recognition mode using an audio input device 45 (i.e., microphone), carried by the portable housing 41 and coupled to the controller 44. Other and/or additional functions may also be activated or removed, for example, some keys (e.g., the shift key) from the keyboard on the touch display 55 may be removed and/or a different keyboard displayed on the touch display. Of course, similar to the embodiments described above, the cloud server 33 may operate in the reverse. That is, if the user's typing speed increases, then the cloud server 33 may add virtual keys or display a different more advanced keyboard on the touch display 55.

Figure 5:
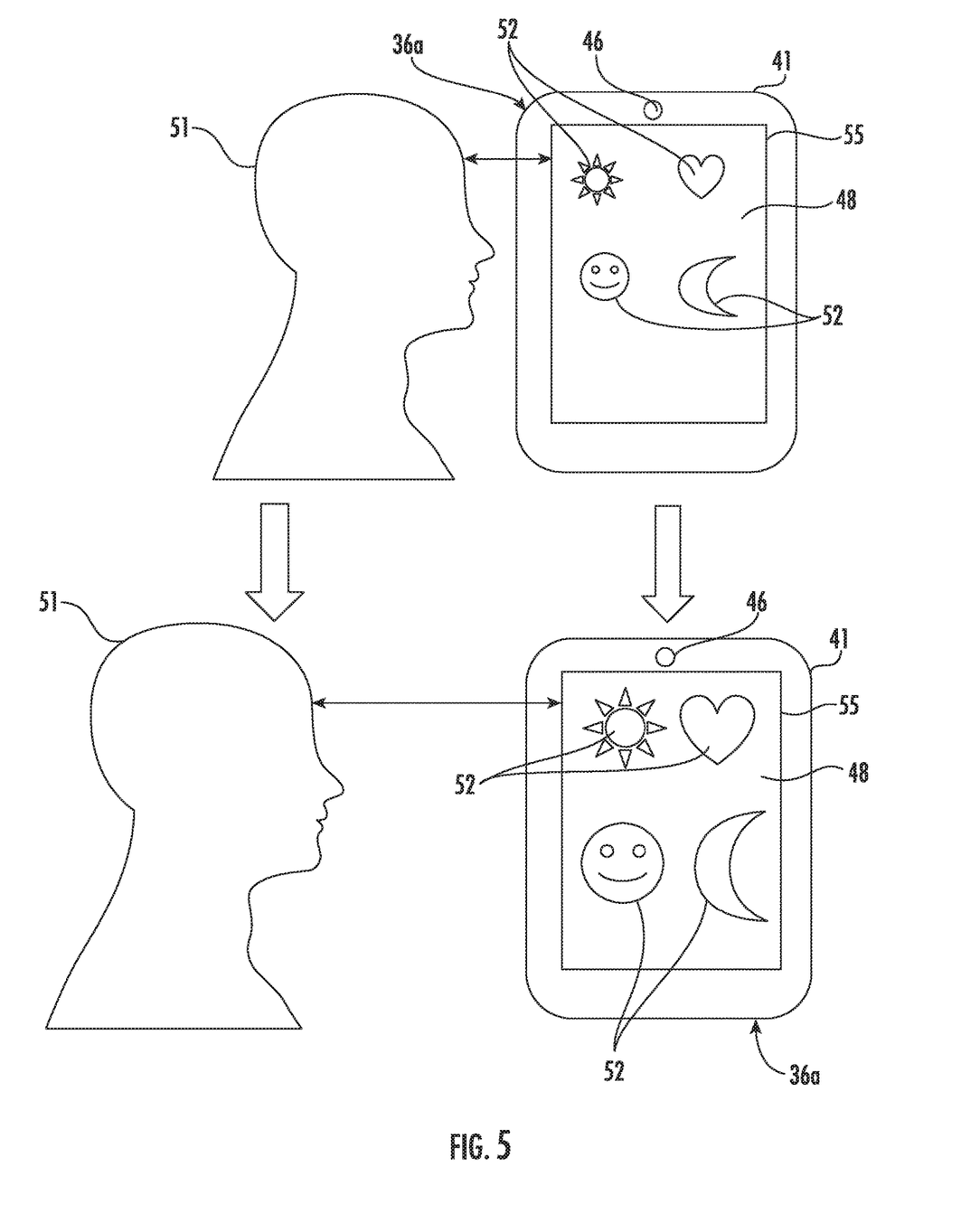
FIG. 5 is an operational diagram of an HA user interface device according to another embodiment.

Referring now additionally to FIG. 5, in another embodiment, the given HA user interface device 36a includes a camera 46 carried by the portable housing 41 and coupled to the controller 44. The camera 46 may cooperate with the controller 44 to measure device-to-user distance data (i.e., the distance from the face of the user 51 to the device), for example. A larger or growingly large distance from the face of the user 51 may be an indication that the user may need reading glasses, for example. Accordingly, the cloud server 33 may determine the user cognitive level based upon a varying or changing distance over a given time period. The HA user interface device 36a, based upon the user cognitive level sent from the cloud server 33, may operate the UI 48 so that the size of elements 52 within the UI on the touch display 55 increase. While a camera 46 is described, it will be appreciated by those skilled in the art that other types of sensors for sensing the user's distance from touch display 55 may be used, for example, one or more proximity sensors.

Figure 6:
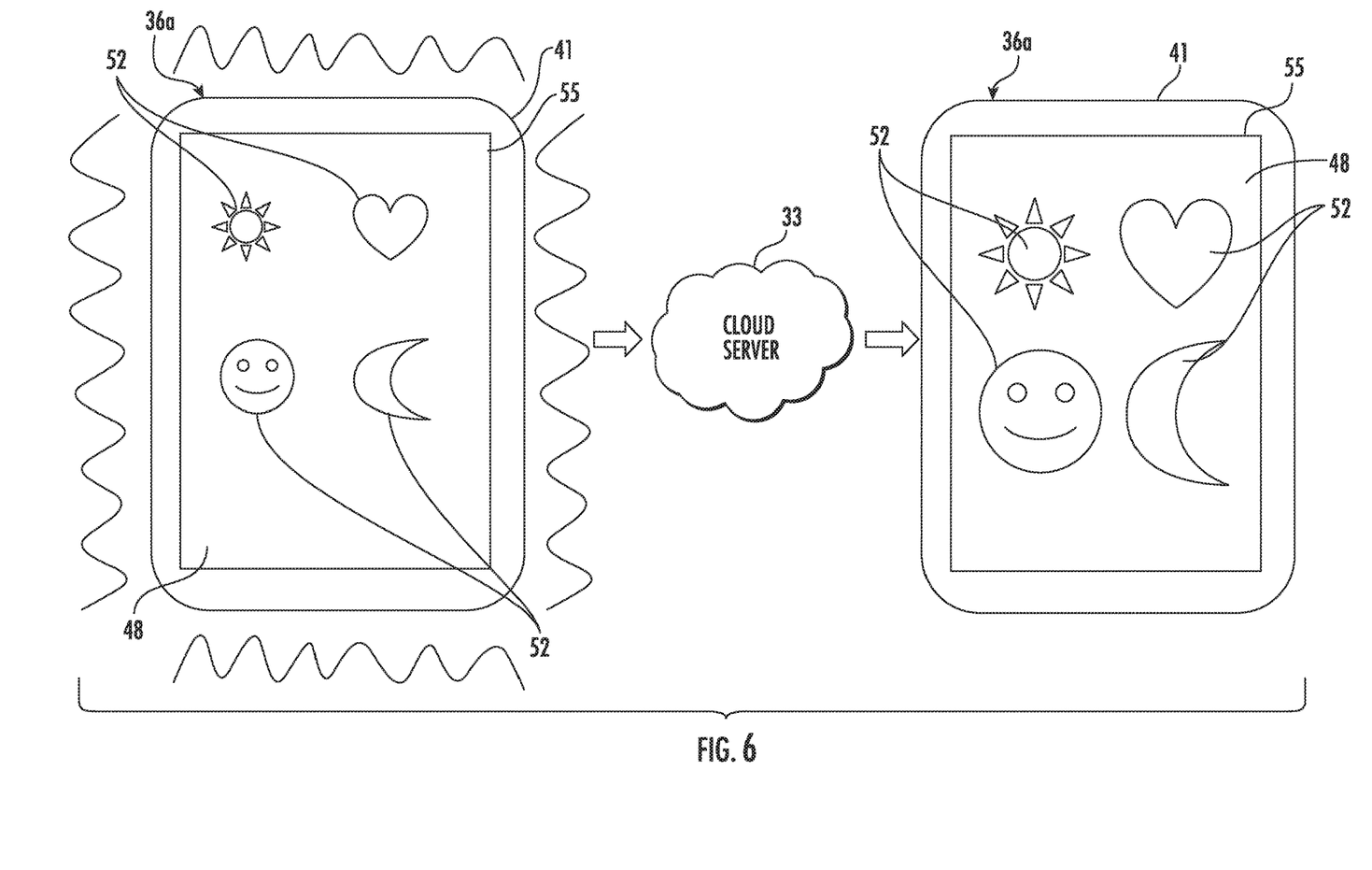
FIG. 6 is an operational diagram of an HA user interface device according to another embodiment.

Referring now additionally to FIG. 6, the HA user interface device 36a may include an accelerometer 47 carried by the portable housing 41 and coupled to the controller 44. The accelerometer 47 may cooperate with the controller 44 to acquire device acceleration data or to detect an acceleration of the portable housing 41, which may correspond to a shaking motion or tremors of the user 51, for example. Accordingly, the cloud server 33 may set the user cognitive level based upon the acceleration, and the user cognitive level received from the cloud server may cause the HA user interface device 36a to increase the size of elements 52 within the UI 48 on the touch display 55 based upon an amount of shaking (e.g., an increased or increasing amount, an amount beyond a threshold).

Figure 7:
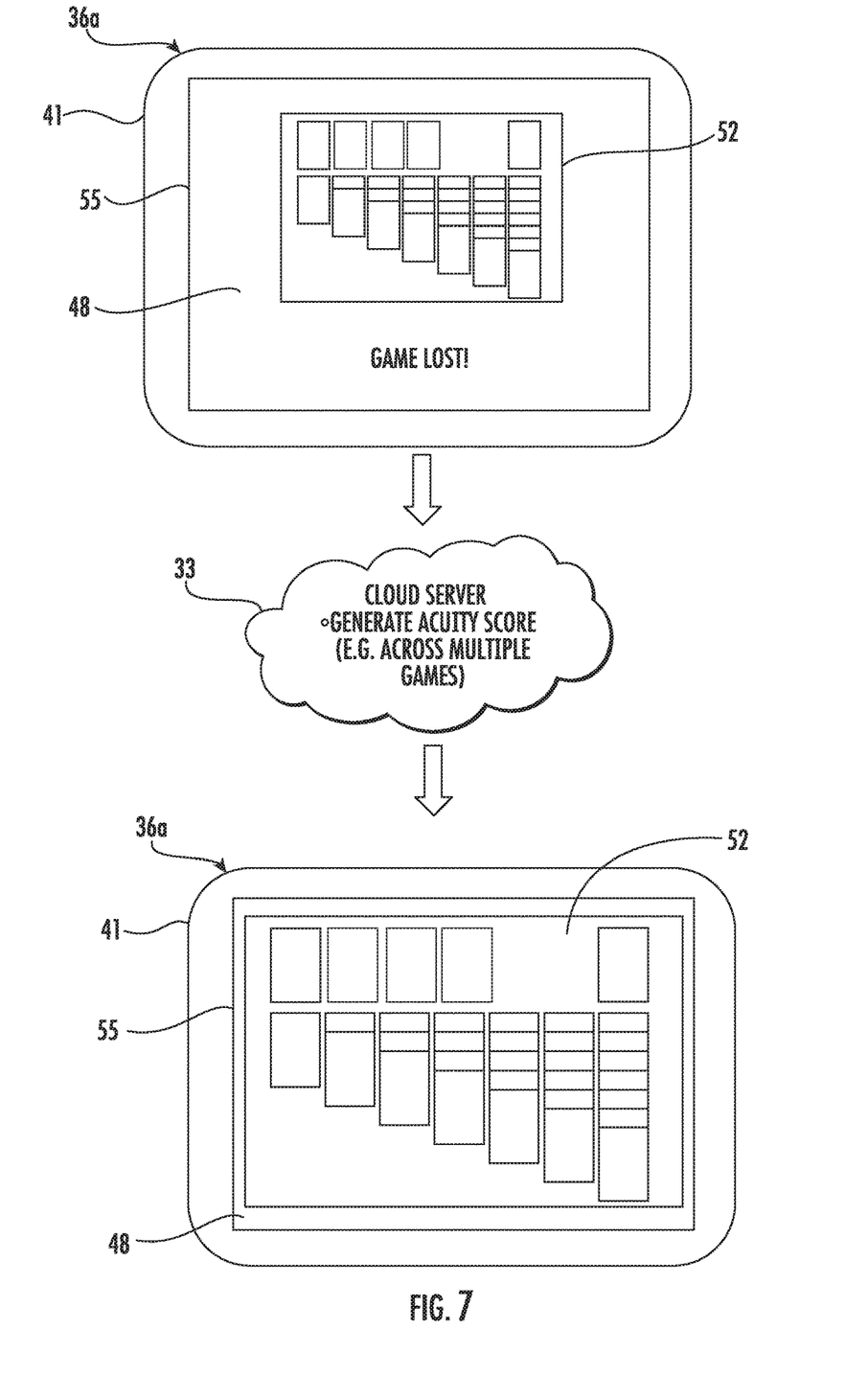
FIG. 7 is an operational diagram of an HA user interface device according to another embodiment.

Referring now additionally to FIG. 7, the user interaction data may include game interaction data. Acuity levels based upon games played on a given HA user interface device 36a-36n may be used as a basis for changing or updating the UI 48 on the touch display 55. For example, if the user 51 is continuously losing in the game of solitaire, this may be an indication of a potential unaddressed health issue. More particularly, the given HA user interface device 36a may communicate the win/loss data to the cloud server 33. The cloud server 33 may generate an acuity score, for example, which may be generated across multiple games and may serve as the basis for the user cognitive level. The cloud server 33 may cause the HA user interface device 36a-36n to adjust the UI 48, for example, make the elements 52 of the UI larger. If the condition continues even after an update of the UI 48, further updates to the UI can be made. The received feedback taken in combination with the types and amount of UI updates may be used to determine the existence of a potential health condition.

While several results of cognitive measures have been described, it will be appreciated that the cloud server 33 may communicate instructions for other and/or additional functions on the HA user interface device 36a-36n. For example, through communication with the cloud server 33, the user cognitive level may determine or cause the HA user interface devices 36a-36n to add or remove functions, access to applications, communications capabilities, change colors within the UI 48, increase or reduce contrast within the UI, adjust brightness within the UI, adjust size of elements 52 within the UI, and adjust touch sensitivity, etc.

Moreover, while the HA system 20 has been described with respect to the cloud server 33 making the UI 48 change or update determination based upon the inputs and communication from the given HA user interface device 36a-36n, it will be appreciated that other devices within the HA system 20 may also determine whether to change and what type of changes to apply to the UI. For example, any given HA user interface device 36a-36n may measure the inputs and determine the UI 48 changes independent of the cloud server. The corresponding HA hub device 34a-34n may also perform these operations.

Interaction data communicated from the HA user interface devices 36a-36n may be processed by the cloud server 33 to generate an alert or notification, for example, of declining cognitive behavior. The notification may be an email, SMS message, or other notification and may be communicated, for example, wirelessly, to one or more of the user, senior living staff, medical staff, and/or family members.

The HA system 20 may be particularly advantageous for predicting changes in cognitive skills, for example, to identify declining health of a user. Additionally, elements of the UI are typically adjusted manually, which may, for a senior user, be relatively difficult. Thus, a senior user may not use or use less of a device that is difficult to operate. The system 20 may address this difficulty by adjusting elements of the UI based upon input over time.

A method aspect is directed to a method of operating a user interface (UI) 48 according to a user cognitive level, the UI defined by a display 43 of a home automation (HA) user interface device 36a-36n for a respective user within a senior living facility 21 from among HA user interface devices in an HA system 20. The HA system includes a cloud server 33, HA operation devices 31a-31n within the senior living facility 21, and HA hub devices 34a-34n within the senior living facility to provide communications for the cloud server 33, the HA user interface devices 36a-36n and the HA operation devices. The method includes using the HA user interface device 34a to send user interaction data to the cloud server 33. The cloud server determines the user cognitive level based upon the user interaction data. The method also includes using the HA user interface device 36a to receive the user cognitive level from the cloud server 33, and operate the UI 48 according to the user cognitive level.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A home automation (HA) system comprising:
    a cloud server;
    a plurality of HA operation devices;
    a plurality of HA user interface devices for respective users and each comprising a user audio input device, a touch display defining a user interface (UI), and a controller coupled to the user audio input device and the touch display, the controller of each HA user interface device being switchable between a voice input mode for receiving user input based upon the user audio input device and a touch input mode for receiving user input based upon the touch display; and
    a plurality of HA hub devices to provide communications for the cloud server, the plurality of HA user interface devices and the plurality of HA operation devices;
    the controller of each HA user interface device configured to send user interaction data to the cloud server and operate the UI according to a user cognitive level, the user interaction data comprising a current touch display user contact location and historical touch display user contact locations; and
    the cloud server configured to
        determine the user cognitive level based upon the user interaction data received from a given HA user interface device,
        decrease the user cognitive level based upon the current touch display user contact location being outside a touch location threshold relative to the historical touch display user contact locations, and
        send the user cognitive level to the given HA user interface device; and
    the controller of each HA user interface device being configured to switch from the touch input mode to the voice input mode based upon the decreased user cognitive level.

2. The HA system of claim 1 wherein the cloud server is configured to decrease the user cognitive level based upon the user interaction data received from the given HA user interface device representing cognitive decline of the user.

3. The HA system of claim 1 wherein the user interaction data comprises time periods between successive user contacts on the touch display.

4. The HA system of claim 1 wherein each HA user interface device comprises a camera; and wherein the user interaction data comprises device-to-user distance data.

5. The HA system of claim 1 wherein each HA user interface device comprises an accelerometer; and wherein the user interaction data comprises device acceleration data.

6. The HA system of claim 1 wherein the user interaction data comprises user game interaction data.

7. The HA system of claim 1 wherein the user cognitive level determines at least one of a color adjustment within the UI, an adjustment in contrast within the UI, an adjustment in brightness within the UI, an adjustment in size within the UI, and a disablement of elements within the UI.

8. A home automation (HA) user interface device from among a plurality thereof for respective users and to be used with an HA system comprising a cloud server, a plurality of HA operation devices and a plurality of HA hub devices to provide communications for the cloud server, the plurality of HA user interface devices, and the plurality of HA operation devices, each HA user interface device comprising:
    a user audio input device;
    a touch display defining a user interface (UI); and
    a controller coupled to the user audio input device and the touch display, the controller being switchable between a voice input mode for receiving user input based upon the user audio input device and a touch input mode for receiving user input based upon the touch display, and configured to send user interaction data to the cloud server, the cloud server determining a cognitive level based upon the user interaction data, the user interaction data comprising a current touch display user contact location and historical touch display user contact locations, the cloud server decreasing the user cognitive level based upon the current touch display user contact location being outside a touch location threshold relative to the historical touch display user contact locations, receive the user cognitive level from the cloud server, operate the UI according to the user cognitive level, and switch from the touch input mode to the voice input mode based upon the decreased user cognitive level.

9. The HA user interface device of claim 8 wherein the user interaction data comprises time periods between successive user contacts on the touch display.

10. The HA user interface device of claim 8 further comprising a camera; and wherein the user interaction data comprises device-to-user distance data.

11. The HA user interface device of claim 8 further comprising an accelerometer; and wherein the user interaction data comprises device acceleration data.

12. The HA user interface device of claim 8 wherein the user interaction data comprises user game interaction data.

13. The HA user interface device of claim 8 wherein the user cognitive level determines at least one of a color adjustment within the UI, an adjustment in contrast within the UI, an adjustment in brightness within the UI, an adjustment in size within the UI, and a disablement of elements within the UI.

14. A method of operating a user interface (UI) according to a user cognitive level, the UI defined by a user audio input device and a touch display of a home automation (HA) user interface device for a respective user from among a plurality of HA user interface devices in an HA system, the HA user interface device being switchable between a voice input mode for receiving user input based upon the user audio input device and a touch input mode for receiving user input based upon the touch display, the HA system comprising a cloud server, a plurality of HA operation devices, and a plurality of HA hub devices to provide communications for the cloud server, the plurality of HA user interface devices and the plurality of HA operation devices, the method comprising:

using the HA user interface device to send user interaction data to the cloud server, the user interaction data comprising a current touch display user contact location and historical touch display user contact locations, the cloud server determining the user cognitive level based upon the user interaction data and decreasing the user cognitive level based upon the current touch display user contact location being outside a touch location threshold relative to the historical touch display user contact locations, receive the user cognitive level from the cloud server, operate the UI according to the user cognitive level, and switch from the touch input mode to the voice input mode based upon the decreased user cognitive level.

15. The method of claim 14 wherein the cloud server decreases the user cognitive level based upon the user interaction data received from the given HA user interface device representing cognitive decline of the user.

16. The method of claim 14 wherein the user interaction data comprises time periods between successive user contacts on the touch display.

17. The method of claim 14 wherein the HA user interface device comprises a camera; and wherein the user interaction data comprises device-to-user distance data.

18. The method of claim 14 wherein the HA user interface device comprises an accelerometer; and wherein the user interaction data comprises device acceleration data.

19. The method of claim 14 wherein the user interaction data comprises user game interaction data.

20. The method of claim 14 wherein the user cognitive level determines at least one of a color adjustment within the UI, an adjustment in contrast within the UI, an adjustment in brightness within the UI, an adjustment in size within the UI, and a disablement of elements within the UI.

* * * * *